United States Patent [19]

Stahl et al.

[11] Patent Number: 5,120,228
[45] Date of Patent: Jun. 9, 1992

[54] INTRINSIC PERCEPTUAL MOTOR TRAINING DEVICE

[76] Inventors: William Stahl, 610 E. Illinois St.; James McMullen, 819 S. Franklin St., both of Mt. Pleasant, Mich. 48858

[21] Appl. No.: 698,846

[22] Filed: May 13, 1991

Related U.S. Application Data

[63] Continuation-in-part of Ser. No. 493,826, Mar. 15, 1990, abandoned.

[51] Int. Cl.⁵ ............................................. G09B 19/00
[52] U.S. Cl. ................................... 434/258; 434/112; 434/255; 128/25 R; 128/782; 273/DIG. 27
[58] Field of Search ............... 434/247, 255, 258, 112, 434/255; 364/413, 522, 559; 272/70, 93; 273/DIG. 27; 128/782, 640, 710, 15 R, 634, 697, 664, 630, 775, 732, 779

[56] References Cited

U.S. PATENT DOCUMENTS

| | | | |
|---|---|---|---|
| 4,375,674 | 3/1983 | Thornton | 364/559 |
| 4,802,484 | 2/1989 | Friedman et al. | 128/630 |
| 4,906,193 | 3/1990 | McMullen et al. | 434/258 |

Primary Examiner—Richard J. Apley
Assistant Examiner—Glenn Richman
Attorney, Agent, or Firm—Terry M. Gernstein

[57] ABSTRACT

An intrinsic perceptual motor training device comprising a data recording apparatus for recording when a patients body moves out of a test area. The data recording apparatus includes a pulse generator that generates a signal pulse whenever a beam of light associated with a test area defining elements is interrupted. The pulse generator is coupled to a strip chart to mark a real time strip chart whenever one of the test area defining beams is interrupted. The pulse generator can also be connected to a computer and the signal pulse used in conjunction with data analysis software.

2 Claims, 5 Drawing Sheets

INTRINSIC PERCEPTUAL MOTOR TRAINING DEVICE

The present disclosure is a continuation-in-part of Ser. No. 07/493,826, filed on Mar. 15, 1990 now abandoned. Accordingly, all disclosure in the just-mentioned patent application is incorporated herein by reference.

TECHNICAL FIELD OF THE INVENTION

The present invention relates to the general art of biomechanics, and to the particular portion of that field relating to motor skills training.

BACKGROUND OF THE INVENTION

If, for some reason, such as injury, insult, surgery, disease, or the like, the neurological functioning of a patient is interrupted, it has been found that such patient loses some portion of his or her ability to recognize the spatial position and orientation of his or her body and/or parts thereof with respect to itself and/or to the surroundings. As discussed in U.S. Pat. No. 4,906,193, the term "interruption of neurological functions" is intended to include, not only the occurrences listed above, but any occurrence that affects the neurological or muscularskeletal system of a patient.

This loss of ability is often manifested in a loss of the ability to properly walk, stand, sit, establish and hold proper posture, or to execute gross motor sequential movements, such as rolling and the like. For example, the stroke or disease may inhibit the patient's ability to walk with a normal gait, or may cause that patient to sit at an angle without knowing of the irregularity. In fact, such a patient may be sitting at an angle with respect to the normal upright orientation and feel as though he is in a perfectly proper position and orientation, or may walk with an extremely exaggerated leg movement thinking that he is executing a normal gait.

For these reasons, as well as others which will be known to those skilled in the art of biomechanics and motor skills training, the field of biomechanics has developed several techniques for retraining such a patient to establish normal body positioning, orientation and movement.

Several examples of such techniques were presented and discussed in the parent patent, as well as in U.S. Pat. No. 4,906,193, the disclosure of which is incorporated herein by reference. The just-mentioned patent discloses a technique that improves upon the motor skill training techniques by training a patient using a non-tactile process. The non-tactile process overcomes most of the disadvantages of known motor skill training techniques.

While extremely effective, the non-tactile motor skill training technique and mechanism disclosed in the incorporated patent and patent application can still be improved in several areas. For example, to be even more effective, the health care provider conducting the retraining process should have an exact record of the prior training sessions. Such a record will enable the health care provider to plan future training sessions by alerting him to special areas of difficulty for the patient. Since many health care providers have many patients, such a record will enable the health care provider to remember the particular patient with an exactness not possible at the present time.

Still further, an accurate record of a training session can be shared among several health care providers so the patient can be analyzed by more than one specialist. Special programs can be devised using techniques that may not be known to one of the health care providers but may be known to another provider.

Additionally, an accurate record of a training session can be used in a data analysis process whereby a health care provider may be able to develop new techniques and publish his or her findings so other health care providers can benefit from his or her experience. Still further, accurate recording of training session responses could be adapted for computer recording whereby a great number of training sessions from a variety of patients could be analyzed to determine the validity of a particular technique, or to develop new techniques and compare the new techniques to other techniques.

Therefore, there is a need for improving the motor training device and method disclosed in U.S. Pat. No. 4,906,913. Specifically, there is a need for improving this device and method by providing means for gathering and recording data associated with one or more training sessions.

OBJECTS OF THE INVENTION

It is a main object of the present invention to improve the device and method disclosed in U.S. Pat. No. 4,906,193 for training and developing motor skills using the intrinsic process disclosed in that patent.

It is another object of the present invention to provide means for recording and gathering data associated with training sessions using the techniques and device of U.S. Pat. No. 4,906,193.

SUMMARY OF THE INVENTION

These, and other, objects are achieved by including a data gathering assembly with the assembly disclosed in U.S. Pat. No. 4,906,193. As disclosed in the patent, the patented device includes a means for generating a beam or field. The beam or field defines the test area, and each beam is incident on a beam receiver. The receiver of the patented device includes means for generating an alarm when the beam or field is interrupted or disturbed.

Specifically, the data gathering assembly of the present invention is connected to the beam receiving elements or to the field of the patented device, and generates a signal whenever a beam or field is interrupted or disturbed. The signal is input into a strip chart recording device, or into a computer, or into a software program that is used by a computer on a real time basis. The training session time is then divided, and the strip chart marked accordingly so the patient movements can be overlaid onto the strip chart for analysis. The strip chart or similar real time recording means, can be used in conjunction with a computer or a computer program to record and analyze the data associated with the training session.

In this manner, the exact details of the training session, including patient reactions, can be recorded for later analysis and compilation. A health care provider will have an accurate record of all training sessions so re-occurring problems will be readily identified and techniques developed to overcome these problems with this patient or with other patients. The data can also be collated and analyzed for papers and the like whereby information can be shared among health care providers.

BRIEF DESCRIPTION OF THE DRAWING FIGURES

FIG. 1 is a side elevational view showing the system embodying the invention disclosed in U.S. Pat. No. 4,906,193 and the improvement thereto according to the present invention.

DETAILED DESCRIPTION OF THE PREFERRED EMBODIMENT OF THE INVENTION

Figure 1:
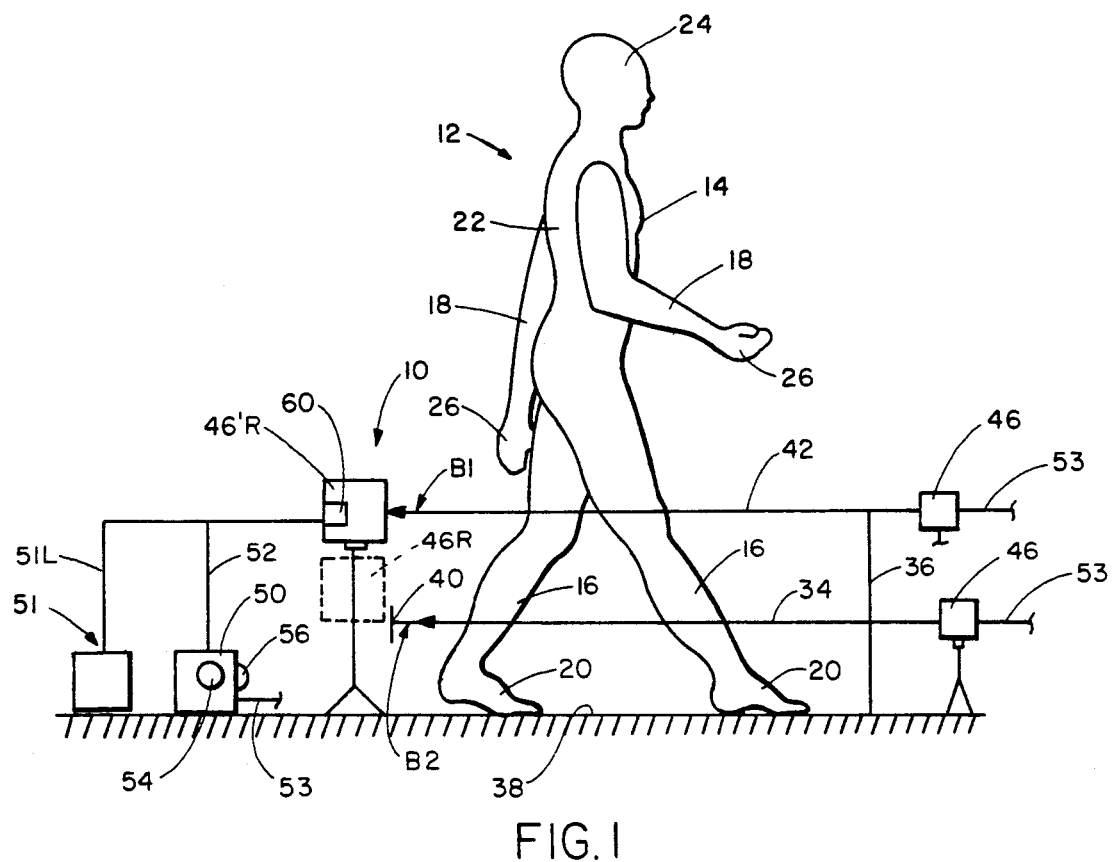
Figure 2:
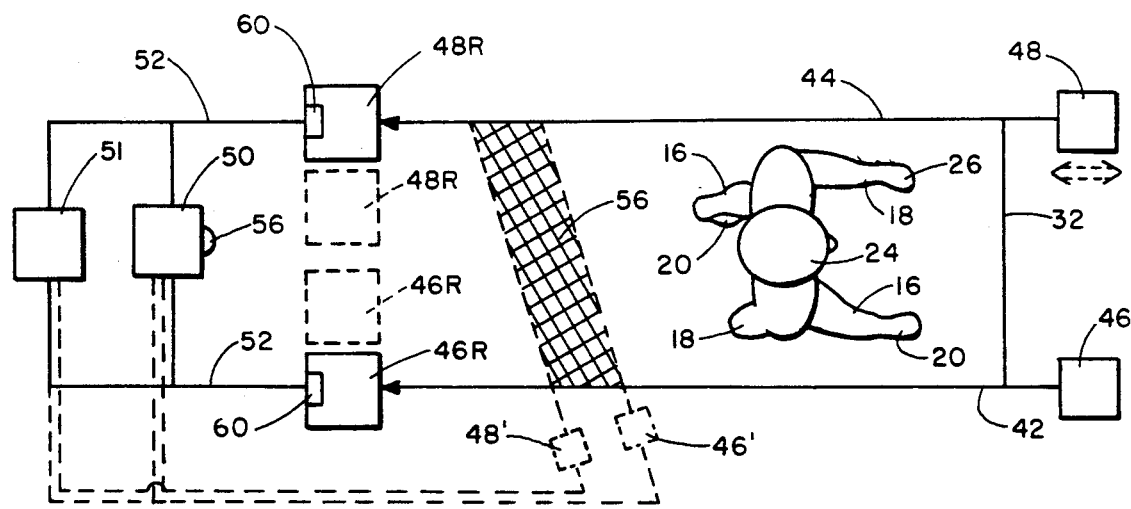
FIG. 2 is a top plan view thereof.

Shown in FIGS. 1 and 2 is a perceptual motor training device 10 for retraining a patient 12 after interruption of the neurological functions of such patient 12 by intrinsically training that patient 12 to recognize the spatial position and/or orientation of his body 14 and/or the parts thereof, such as his legs 16, arms 18, feet 20, trunk 22, head 24, hands 26 or any other parts of his or her body as is known to those skilled in the art, with respect to the remainder of his or her body. It is noted that FIGS. 1 and 2 have been drawn to illustrate a walking process, and thus do not exactly agree.

The device 10 includes a means for defining a test area, such as a path which is being traversed by the patient 12 in FIGS. 1 and 2. The test area has spatial limits, such as width 32, length 34 and height 36 as well as orientation, prescribed according to the desired functional and operational requirements of the particular motor function for which the patient is being retrained and/or tested. The path in FIGS. 1 and 2 is horizontal in its axial extent, and has a height measured from floor 38, and is used to retrain a patient in his or her walking skills. The test area shown in FIGS. 1 and 2 has an axial extent of undetermined length beginning at origin 40, but could be finite in length beginning at origin 40, as was discussed in the incorporated patent.

The test area is defined by beams or field extremities, as was discussed in the incorporated patent, and such test area extremities are shown in FIGS. 1 and 2 by reference indicators 42 and 44. The beams and/or fields are generated by generators 46 and 48 and receivers 46R and 48R all of which are adjustable in at least two planes, such as the vertical plane indicated in single chain dots in FIG. 1, as well as in the horizontal plane as indicated in the double chain dots in FIG. 2. Other adjustments, such as angular, can be made as well to orient the test area as necessary. Beams from the generators are indicated in FIGS. 1 and 2 by arrows B1 and B2, and are incident on the beam receivers 46R and 48R respectively. The receivers are connected to a control/alarm unit 50 by leads 52, and the control/alarm unit 50 includes an audible alarm 54, such as a bell and/or a visual alarm 56, such as a light. The control/alarm unit 50 has suitable circuitry for operating and controlling the generators 46 and 48, and for setting the intensity of both the test area extremity defining beams and fields and the alarm as necessary and are connected to the generators by leads, such as lead 53.

The extremity defining means indicated at 42 and 44, the generators 46 and 48, the beam receivers 46R and 48R, the circuitry in unit 50 coupling the receivers and the generators to the alarm means and the alarm means 50 are part of a means for determining when the spatial position and/or orientation of the patient's body and/or parts thereof are in error with regard to a desired spatial position and/or orientation in the particular retraining and/or testing, and signalling the patient and the health care provider in a non-tactile manner whenever a portion of the patient's body moves out of the test area. Thus, for example, during a gait training procedure, should one of the patient's legs swing in an undesired manner, that leg will move out of the test area and break the beam or disturb the field as defined by the test area extremity indicators 42 and 44. If a field is used, that field will extend from the floor 38 to the desired height and any movement of the leg outside the path will disturb the field. On the other hand, should a beam be used, the height of the beam is set and the leg can move under the beam without interrupting the beam, but will interrupt the beam if it move at the beam height. The beam is thus set by the therapist according to the particular parameters of the training process and session.

Figure 3:
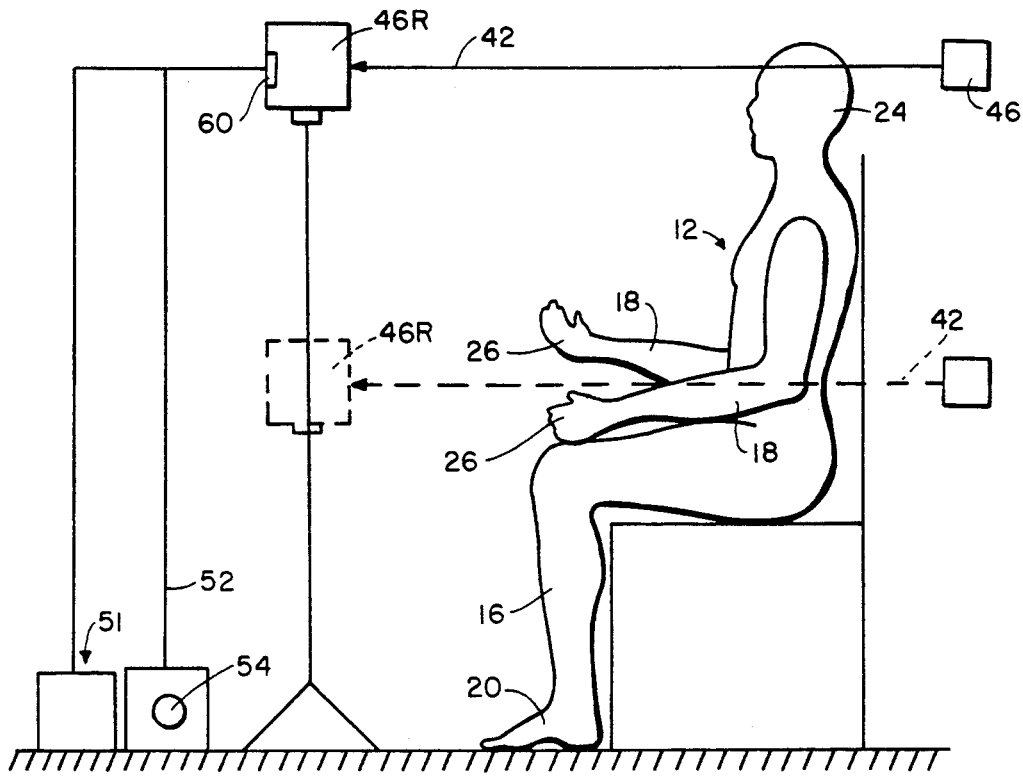
FIG. 3 is an elevational view thereof in conjunction with a patient being trained to sit with proper posture.
Figure 4:
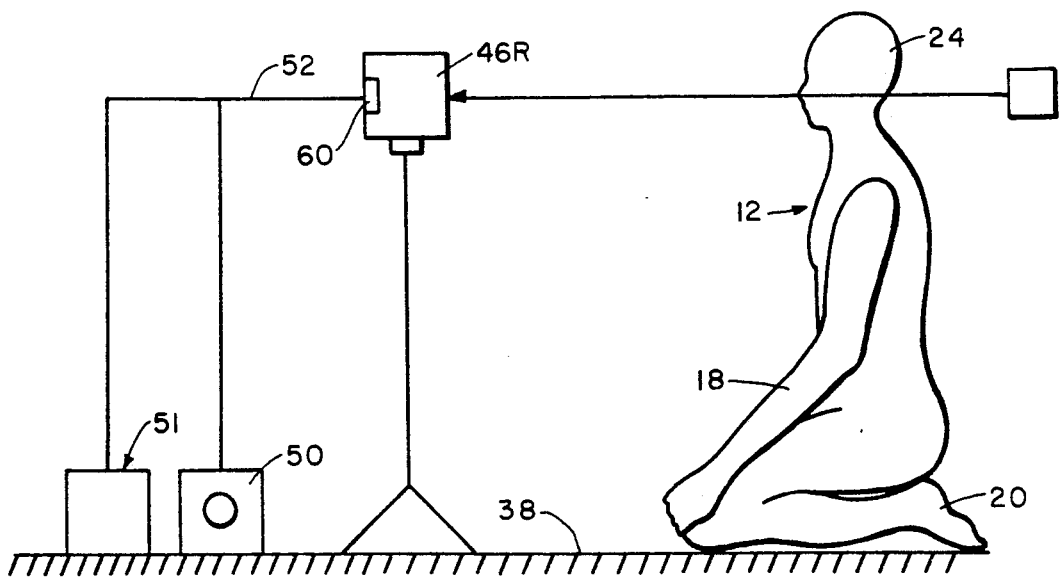
FIG. 4 is an elevational view thereof in conjunction with a patient being trained to kneel with proper posture.
Figure 5:
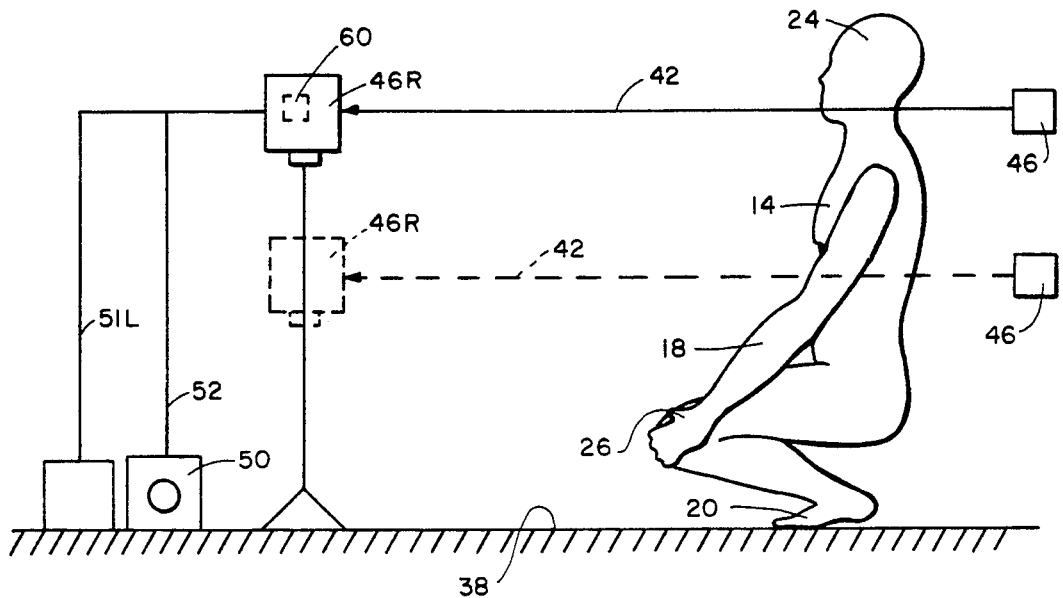
FIG. 5 is an elevational view thereof in conjunction with a patient being trained to squat with proper posture.

As discussed in the incorporated patent, the beams and fields can be used to train and teach sitting posture (FIG. 3), kneeling posture (FIG. 4), squatting posture (FIG. 5) or the like. Various parts of the body can also be monitored, such as head position, hand and arm position and movement, and the like. These elements of a training session are identified and monitored by appropriately locating the beam generators and receivers or the field generators and developing the movements and positions that will be required of the patient during the session.

Once the field is disturbed or the beam interrupted, the receivers have a signal generating means therein to indicate that the field has been disturbed or the beam interrupted, as will be discussed below. The signal is then sent to the control unit 50 and to a recording unit 51 connected to the signal generators and/or to the signal receivers as by leads 51L and 52, to signal the patient and the therapist of an error by the patient, and to record that event.

A real time record of a training session is kept in the recording unit 51, and the therapist can analyze the data in that record to analyze the training session and plan other sessions.

Figure 6:
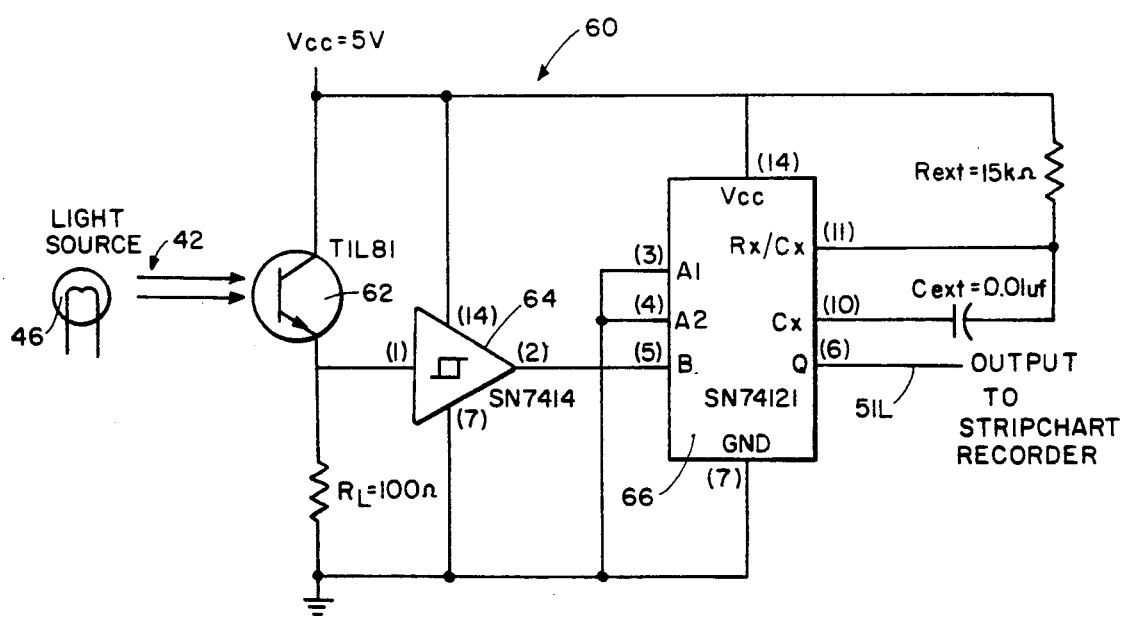
FIG. 6 is a schematic of a pulse generator that generates a signal when a beam is interrupted, with the signal being used by a strip chart recorder to mark a time line whenever a patient moves a part of his or her body out of a desired test area during a training session.
Figure 8:
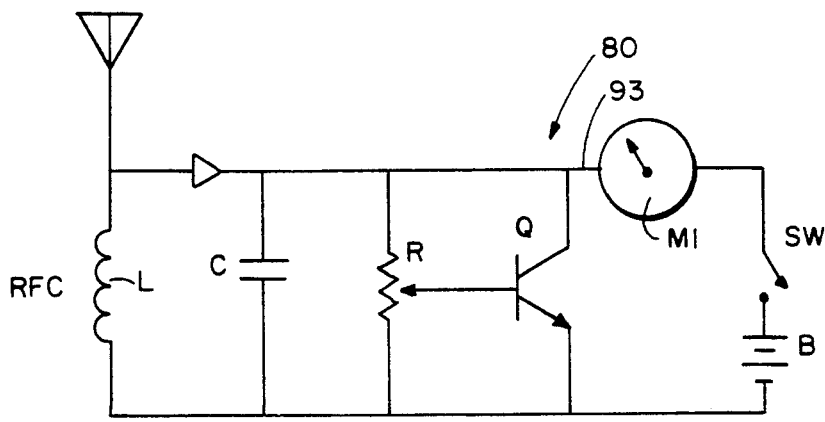
FIG. 8 is a schematic showing a circuit that is used to emit a signal when a field is used to define a test area.
Figure 9:
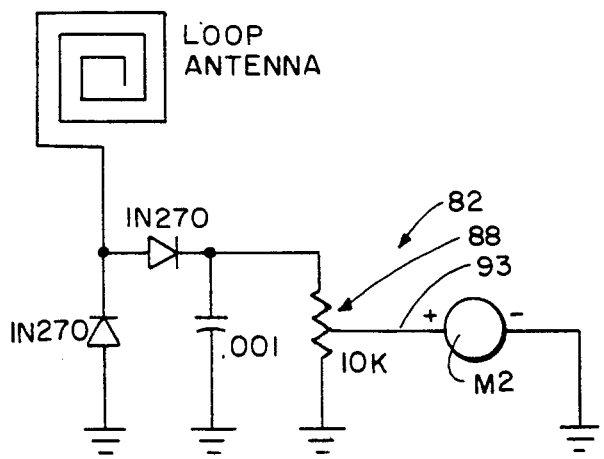
FIG. 9 is a schematic showing another circuit that is used to emit a signal when a field is used to define a test area.
Figure 10:
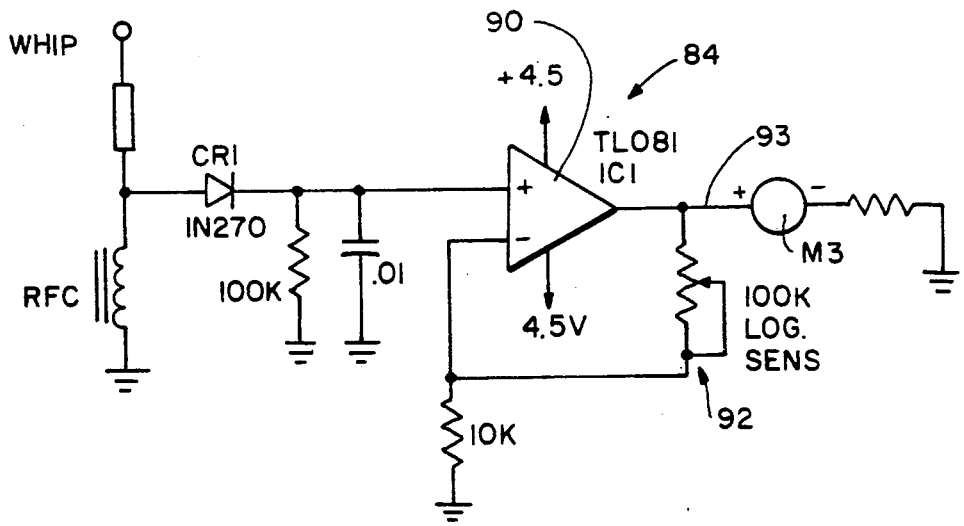
FIG. 10 is a schematic showing another circuit that is used to emit a signal when a field is used to define a test area.
Figure 7:
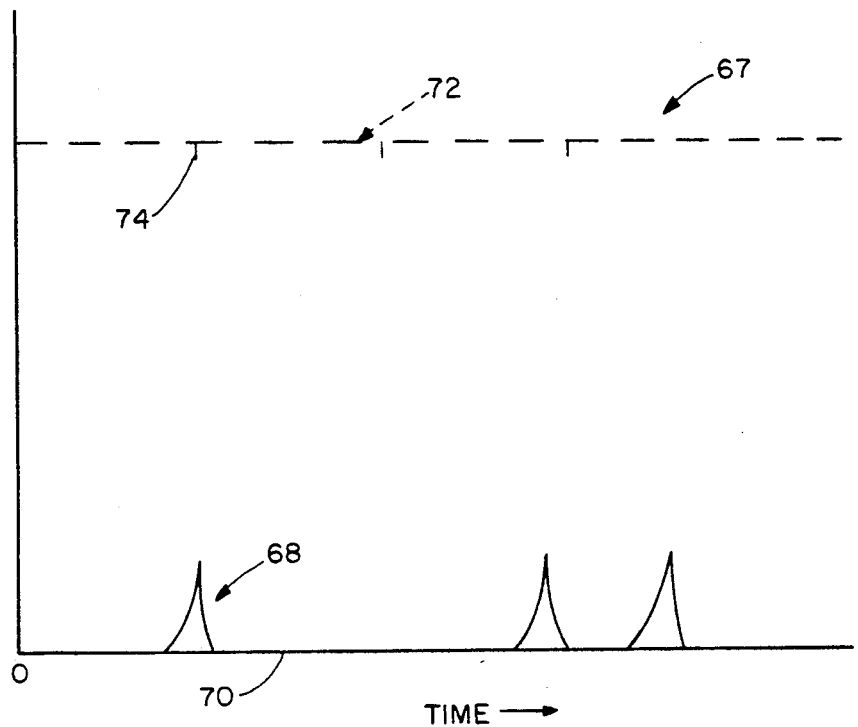
FIG. 7 is a strip chart record generated at a training session in conjunction with an overlay associated with the desired movements required of the patient.

Shown in FIGS. 6 and 7 is a recording means that is used in conjunction with the beam receivers or in conjunction with the field to record training session data. The recording means includes a pulse generator 60 located in each of the beam receivers 46 and 48. The pulse generator 60 generates a signal pulse on line 51L whenever the beam 42 is interrupted.

As shown in FIG. 6, the pulse generator 60 includes a phototransistor 62 that is kept on when a light beam from generator 46 or 48 is incident thereon. The phototransistor 62 is located adjacent to any other beam receiving elements used in the device whereby the beam 42 can be incident on all beam receiving elements that are used in the device. Alternatively, mirrors and beam splitting elements can be included so the beams will be incident on all necessary elements. Maintaining the phototransistor 62 on produces a high-logic level voltage at Schmitt-trigger inverter 64, and a TTL-compatible low logic level at pin 5 of monostable 66. When an object, such as a patient's leg, interrupts the beam, the phototransistor turns off the Schmitt-trigger inverter to trigger a signal pulse on line 51L.

The signal pulse from the pulse generator 60 is applied to an input lead of a strip chart recorder and causes a needle on that strip chart recorder to jump. A strip chart 67 is illustrated in FIG. 7, and various jumps, such as initial jump 68, are recorded on the strip chart, and time is also recorded on that strip chart along an axis 70. The time of the jumps can be read from the strip chart, and an overlay 72 can be placed on the strip chart to match the jumps to the positions and movements attempted by the patient during a training session. The overlay 70 includes marks, such as mark 74, at particular times that indicate what movement or position the patient was asked to perform at that particular time. In the example illustrated in FIG. 7, mark 74 indicates a walking movement of a patient's left leg, and jump 68 indicates that the left leg went out of the test area just after the movement began. This indicates that the leg moved out of the test area as it was being brought forward in the walking movement. The therapist now has a record that the patient moved his or her leg improperly in nearly every instance, and can design further training sessions based on such knowledge.

The pulse signal generated by the generator 60 can also be input into a computer and appropriate software used to generate a time dependent curve and to overlay the training session onto that curve. The software can also include subroutines to manipulate the data in a manner desired by the therapist.

In the event that the patented device is used in conjunction with field generators to define the test area, the means for generating a signal whenever the patient moves outside of the test area includes circuits 80, 82 or 84 that include elements M1, M2 and M3 respectively. The circuits can be located anywhere in the field, just so a portion of the circuit is located in the field. In one form of the device, the circuits can even be located in place of circuits 60 in the receivers 46R and 48R. The elements M1, M2 and M3 emit a signal when the field defining the test area is altered, as by having one of the patient's limbs interrupt the field. The elements M1, M2 or M3 can be meters that are connected to a circuit that generates a signal whenever the meter reads a particular level.

In the circuit 80, the tuning range is determined by coil L dimensions and setting of C1. Coils can be plugged in for multirange use or soldered in place if only limited frequency range is of interest.

The circuit 82 includes a potentiometer 88 to adjust the attenuation of the element M2. In circuit 84, an op amp 90 is used to increase sensitivity, and a potentiometer 92 is used to adjust sensitivity.

Figure 11A:
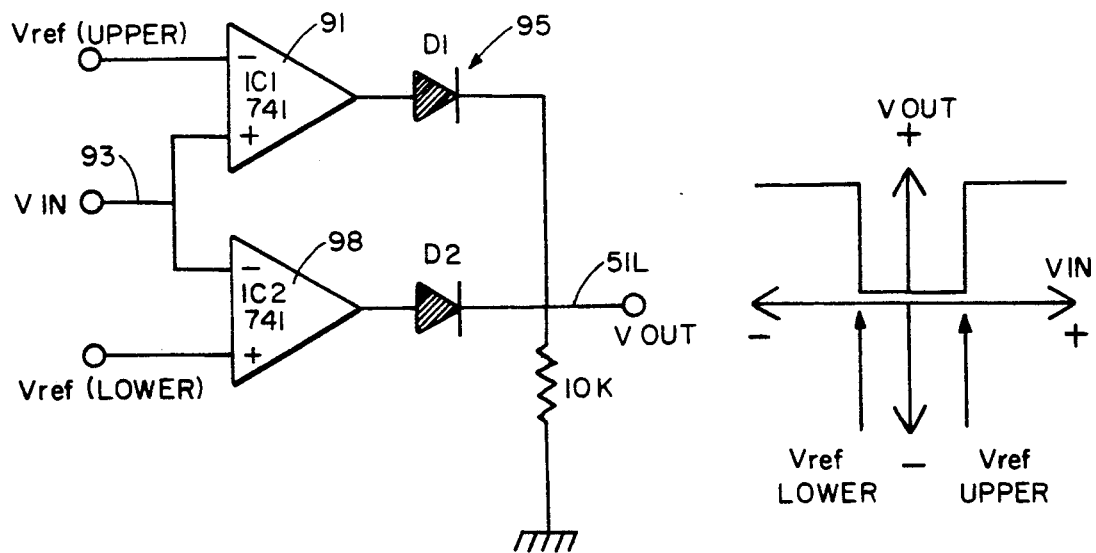
FIG. 11A is a schematic of a window comparator that is used in conjunction with the field testing circuits to generate a signal when a patient disturbs a test area defining field thereby indicating that the patient or part of the patient has moved outside of the test area.
Figure 11B:
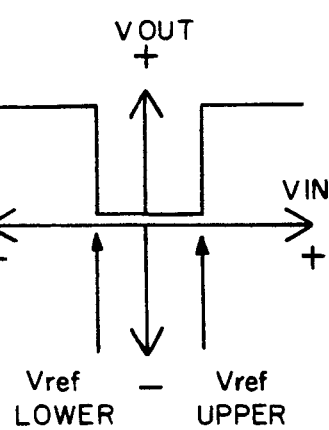
FIG. 11B illustrates the actions of the window comparator shown in FIG. 11A.

Shown in FIGS. 11A and 11B is a circuit 95 that is suitable for use in conjunction with the elements M1, M2 and M3 to generate a pulse signal that is input to a strip chart recorder as above discussed in regard to the circuit 60. The circuit 85 shown in FIG. 11 is a window comparator and provides an output pulse signal on line 51L when an input voltage on line 93 in circuits 80, 82 and 84 lies in between two specified voltages. When the voltage is outside a window, the output on line 51L is positive. The two op amps 96 and 98 are used as voltage comparators. When Vin is more positive than Vref (upper) the output of op amp 96 is positive and D1 is forward biased. Otherwise, the output is negative, D1 is reverse biased and hence Vout is 0 V. Similarly, when Vin is more negative than Vref (lower), the output of the op amp 98 is forward biased and this Vout is positive. Otherwise Vout is 0 V. When Vin lies within the window set by the reference voltages Vout is 0 V. The action of the circuit 95 is illustrated in FIG. 11B. Using these devices, the sensitivity of the alarm means can be adjusted. The output of the meters or the just-described window comparator can also be connected to a strip chart recorder as above discussed, or can be connected directly to a computer so a software program in the computer can analyze and collate the data associated with the field-defined test area boundaries.

It is understood that while certain forms of the present invention have been illustrated and described herein, it is not to be limited to the specific forms or arrangements of parts described and shown.

We claim:

1. In a perceptual motor training device comprising means for retraining a patient after interruption of the neurological functions of such patient by intrinsically training that patient to recognize the spatial position and orientation of a particular body part relative to other parts of his body, with that means including test area defining means for defining a test area which has the spatial limits and orientation thereof prescribed according to desired spatial limits of the particular body part relative to other parts of the patient's body for a particular motor function for which the patient is being retrained and/or tested, with the test area defining means including two reference beam generators each of which generates a beam for defining a first portion of the test area and two beam receivers for determining when the spatial position and/or orientation of the particular body parts relative to other parts of that patient's body are in error with regard to a desired spatial position and/or orientation of the particular body parts relative to other parts of the patient's body in the particular retraining and/or testing, each beam receiver being oriented to receive a beam generated by each of said two beam generators, and signal generating means coupled to each of said beam receivers for signalling the patient in a non-tactile manner whenever the particular body part of the patient's body associated with the particular motor function being tested and/or trained interrupts one of said beams, the improvement in combination therewith comprising:

recording means for recording whenever a patient's body part moves out of the test area, said recording means including a pulse signal generating means coupled to the beam receiving means and generating a pulse signal whenever the beam is interrupted, said pulse signal generating means includes a phototransistor located to have at least one of the beams generated by the beam generators incident thereon, a Schmitt—trigger inverter connected to said phototransistor, and a monostable connected to said Schmitt—trigger inventer.

2. The improvement defined in claim 1 wherein said recording means further includes a strip chart recorder connected to said monostable.

* * * * *